US00PP24368P2

(12) United States Plant Patent
Jepsen

(10) Patent No.: US PP24,368 P2
(45) Date of Patent: Apr. 1, 2014

(54) ***KALANCHOE* PLANT NAMED 'JOYCE'**

(50) Latin Name: *Kalanchoe blossfeldiana*
Varietal Denomination: Joyce

(75) Inventor: Knud Jepsen, Hinnerup (DK)

(73) Assignee: Knud Jepsen A/S, Hinnerup (DK)

( * ) Notice: Subject to any disclaimer, the term of this patent is extended or adjusted under 35 U.S.C. 154(b) by 147 days.

(21) Appl. No.: 13/506,076

(22) Filed: Mar. 24, 2012

(51) Int. Cl.
*A01H 5/00* (2006.01)

(52) U.S. Cl.
USPC ..... Plt./338

(58) Field of Classification Search
USPC ..... Plt./338, 335
See application file for complete search history.

*Primary Examiner* — June Hwu
(74) *Attorney, Agent, or Firm* — C. A. Whealy

(57) ABSTRACT

A new and distinct cultivar of *Kalanchoe* plant named 'Joyce', characterized by its medium plant size; upright, uniform and moderately vigorous growth habit; medium-sized dark green-colored leaves with crenate margins; uniform and freely flowering habit; single medium-sized yellow orange-colored flowers with darker yellow orange-colored throats; and excellent postproduction longevity.

2 Drawing Sheets

Botanical designation: *Kalanchoe blossfeldiana.*
Cultivar denomination: 'JOYCE'.

BACKGROUND OF THE INVENTION

The present invention relates to a new and distinct cultivar of *Kalanchoe* plant, botanically known as *Kalanchoe blossfeldiana*, and hereinafter referred to by the name 'Joyce'.

The new *Kalanchoe* plant is a product of a planned breeding program conducted by the Inventor in Hinnerup, Denmark. The objective of the breeding program is to create new uniform *Kalanchoe* plants with attractive foliage and flower coloration.

The new *Kalanchoe* plant originated from a cross-pollination made by the Inventor in Hinnerup, Denmark in March, 2008 of a proprietary selection of *Kalanchoe blossfeldiana* identified as code number KJ 2002 1358, not patented, as the female, or seed parent with *Kalanchoe blossfeldiana* 'Sarah', disclosed in U.S. Plant Pat. No. 18,928, as the male, or pollen, parent. The new *Kalanchoe* plant was discovered and selected by the Inventor as a single flowering plant from within the progeny of the stated cross-pollination in a controlled greenhouse environment in Hinnerup, Denmark in December, 2008.

Asexual reproduction of the new *Kalanchoe* plant by vegetative terminal cuttings in a controlled greenhouse environment in Hinnerup, Denmark since March, 2009 has shown that the unique features of this new *Kalanchoe* plant are stable and reproduced true to type in successive generations.

SUMMARY OF THE INVENTION

Plants of the new *Kalanchoe* have not been observed under all possible environmental conditions and cultural practices. The phenotype may vary somewhat with variations in environmental conditions such as temperature, daylength and light intensity without, however, any variance in genotype.

The following traits have been repeatedly observed and are determined to be the unique characteristics of 'Joyce'. These characteristics in combination distinguish 'Joyce' as a new and distinct *Kalanchoe* plant:

1. Medium plant size; upright, uniform and moderately vigorous growth habit.
2. Medium-sized dark green-colored leaves with crenate margins.
3. Uniform and freely flowering habit.
4. Single medium-sized yellow orange-colored flowers with darker yellow orange-colored throats.
5. Excellent postproduction longevity.

Plants of the new *Kalanchoe* can be compared to plants of the female parent selection. Plants of the new *Kalanchoe* differ primarily from plants of the female parent selection in plant habit as plants of the new *Kalanchoe* are more uniform than plants of the female parent selection.

Plants of the new *Kalanchoe* can be compared to plants of the male parent, 'Sarah'. Plants of the new *Kalanchoe* differ primarily from plants of 'Sarah' in flower color as plants of 'Sarah' have orange red-colored flowers. In addition, plants of the new *Kalanchoe* have leaves with crenate margins whereas plants of 'Sarah' have leaves with serrate and undulate margins.

Plants of the new *Kalanchoe* can be compared to plants of *Kalanchoe blossfeldiana* 'Ingrid', disclosed in U.S. Plant Pat. No. 18,283. Plants of the new *Kalanchoe* differ from plants of 'Ingrid' in the following characteristics:

1. Plants of the new *Kalanchoe* and 'Ingrid' differ in leaf shape as plants of the new *Kalanchoe* have leaves with cuneate bases and crenate margins whereas plants of 'Ingrid' have leaves with rounded bases and more deeply crenate margins.
2. Plants of the new *Kalanchoe* and 'Ingrid' differ in flower color as plants of 'Ingrid' have light yellow-colored flowers.

BRIEF DESCRIPTION OF THE PHOTOGRAPHS

The accompanying colored photographs illustrate the overall appearance of the new *Kalanchoe* plant showing the colors as true as it is reasonably possible to obtain in colored reproductions of this type. Colors in the photographs may differ slightly from the color values cited in the detailed botanical description which accurately describe the colors of the new *Kalanchoe* plant.

The photograph on the first sheet comprises a side perspective view of a typical flowering plant of 'Joyce' grown in a container.

The photograph on the second sheet comprises close-up views of typical vegetative (upper left) and generative (upper right) leaves; upper (center left) and side (center right) perspective views of typical flowers; and side perspective views of a typical flowering stems (bottom) of 'Joyce'.

DETAILED BOTANICAL DESCRIPTION

The aforementioned photographs and following observations, measurements and values describe plants grown during the summer and autumn in 10-cm containers in a glass-covered greenhouse in Hinnerup, Denmark and under environmental conditions and cultural practices which closely approximate commercial *Kalanchoe* production. During the production of the plants, day temperatures averaged 19° C., night temperatures averaged 21° C. and light levels ranged from 10 kilolux to 50 kilolux. Unrooted cuttings were directly stuck in 10-cm containers and received long day/short night conditions (more than 14 hours of light) for four weeks; plants then received photoinductive short day/long night conditions (minimum 14 hours darkness) until flowering. Plants were 16 weeks old when the photographs and the description were taken. In the detailed description, color references are made to The Royal Horticultural Society Colour Chart, 2007 Edition, except where general terms of ordinary dictionary significance are used.

Botanical classification: *Kalanchoe blossfeldiana* 'Joyce'.

Parentage:

*Female, or seed, parent*.—Proprietary selection of *Kalanchoe blossfeldiana* identified as code number KJ 2003 1358, not patented.

*Male or pollen parent*.—*Kalanchoe blossfeldiana* 'Sarah', disclosed in U.S. Plant Pat. No. 18,928.

Propagation:

*Type*.—By vegetative terminal cuttings.

*Time to initiate roots, summer*.—About two weeks at temperatures of 19° C. to 21° C.

*Time to initiate roots, winter*.—About three weeks at temperatures of 19° C. to 21° C.

*Time to produce a rooted young plant, summer*.—About three weeks at temperatures of 19° C. to 21° C.

*Time to produce a rooted young plant, winter*.—About 24 days at temperatures of 19° C. to 21° C.

*Root description*.—Fine, fibrous; white in color.

*Rooting habit*.—Freely branching; medium density.

Plant description:

*Plant habit*.—Upright, uniform and moderately vigorous growth habit.; very freely flowering with numerous compound cymes; inverted triangle with rounded crown; appropriate for 6 to 13-cm containers.

*Plant height at flowering*.—About 18 cm to 23 cm.

*Plant diameter at flowering*.—About 17 cm to 20 cm.

*Branching habit*.—About three to five lateral branches develop per plant; pinching (removal of the terminal apex) is not required but will enhance lateral branch development.

Lateral branch description:

*Length*.—About 10 cm to 16 cm.

*Diameter*.—About 5 mm.

*Internode length*.—About 3 cm to 5 cm.

*Aspect*.—Erect.

*Strength*.—Strong.

*Texture*.—Smooth, glabrous.

*Color*.—Close to 146B.

Foliage description:

*Arrangement*.—Opposite, simple; generally symmetrical.

*Length*.—About 9 cm to 12 cm.

*Width*.—About 5 cm to 8 cm.

*Shape*.—Ovate.

*Apex*.—Obtuse.

*Base*.—Cuneate.

*Margin*.—Crenate; crenations, shallow to medium.

*Texture, upper and lower surfaces*.—Glabrous, leathery; succulent.

*Venation pattern*.—Pinnate.

*Color*.—Developing and fully expanded leaves, upper surface: Close to 147A; venation, close to 147A. Developing and fully expanded leaves, lower surface: Close to 147B; venation, close to 147B.

*Petiole*.—Length: About 5 mm to 10 mm. Diameter: About 5 mm to 8 mm. Texture, upper and lower surfaces: Smooth, glabrous. Color, upper surface: Close to 147A. Color, upper surface: Close to 147B.

Flower description:

*Flower arrangement and flowering habit*.—Single flowers arranged in compound dichasial cymes that arise from leaf axils; uniform and freely flowering habit with usually about 20 to 70 flowers developing per inflorescence.

*Fragrance*.—None detected.

*Flowering response*.—Under short day/long night photoinductive conditions, about 67 (summer) to 103 (winter) days are required; actual time to flower is primarily dependent upon temperature and light intensity.

*Post-production longevity*.—Excellent post-production longevity; plants maintain good foliage and flower substance for about six weeks under interior environmental conditions; flowers persistent.

*Flower buds*.—Shape: Ellipsoidal. Length: About 1.8 cm. Diameter: About 4 mm. Color: Close to 10A.

*Inflorescence height*.—About 6 cm to 12 cm.

*Inflorescence diameter*.—About 3 cm to 6 cm.

*Flower diameter*.—About 1.6 cm to 1.8 cm.

*Flower length* (*height*).—About 1.3 cm.

*Petals*.—Arrangement: About four in a single whorl fused at the base. Length: About 1 cm. Width: About 8 mm. Aspect: Upright to eventually perpendicular to the pedicel. Shape: Orbicular. Apex: Mucronate. Margin: Entire. Texture, upper and lower surfaces: Smooth, glabrous. Color: When opening, upper surface: Lobe, close to 17A; throat, close to 23A. When opening, lower surface: Close to 12B. Fully opened, upper surface: Lobe, close to 16A; throat, close to 23B; lobe color becoming closer to 16B with development. Fully opened, lower surface: Close to 12B.

*Sepals*.—Appearance: Four fused at the base. Length: About 9 mm. Width: About 2 mm. Shape: Lanceolate. Apex: Acute. Base: Truncate. Margin: Entire. Texture, upper and lower surfaces: Smooth; glabrous. Color, upper and lower surfaces: Close to 146B.

*Peduncles*.—Length: About 2 cm to 8 cm. Diameter: About 5 mm. Aspect: Erect to about 60° from vertical. Strength: Strong. Texture: Smooth, glabrous. Color: Close to 146C.

*Pedicels*.—Length: About 2 mm to 10 mm. Diameter: About 2 mm. Aspect: Erect to about 90° from vertical. Strength: Strong. Texture: Smooth, glabrous. Color: Close to 146C.

*Reproductive organs*.—Androecium: Stamen number: About eight per flower. Anther shape: Elliptic to oblong. Anther size: About 0.4 mm by 0.8 mm. Anther color: Close to 22B. Amount of pollen: Moderate. Pollen color: Close to 3B. Gynoecium: Pistil number: About four per flower. Pistil length: About 1.1 cm. Style length: About 3 mm. Style color: Close to N145A. Stigma shape: Round. Stigma color: Close to N145A. Ovary color: Close to 144A.

*Seeds and fruits*.—Seed and fruit development have not been observed on plants of the new *Kalanchoe*.

Temperature tolerance: Plants of the new *Kalanchoe* have been observed to tolerate temperatures from about 5° C. to about 30° C.

Pathogen & pest resistance: Plants of the new *Kalanchoe* have not been observed to be resistant to pests and pathogens common to *Kalanchoes*.

It is claimed:

1. A new and distinct *Kalanchoe* plant named 'Joyce' as illustrated and described.

* * * * *

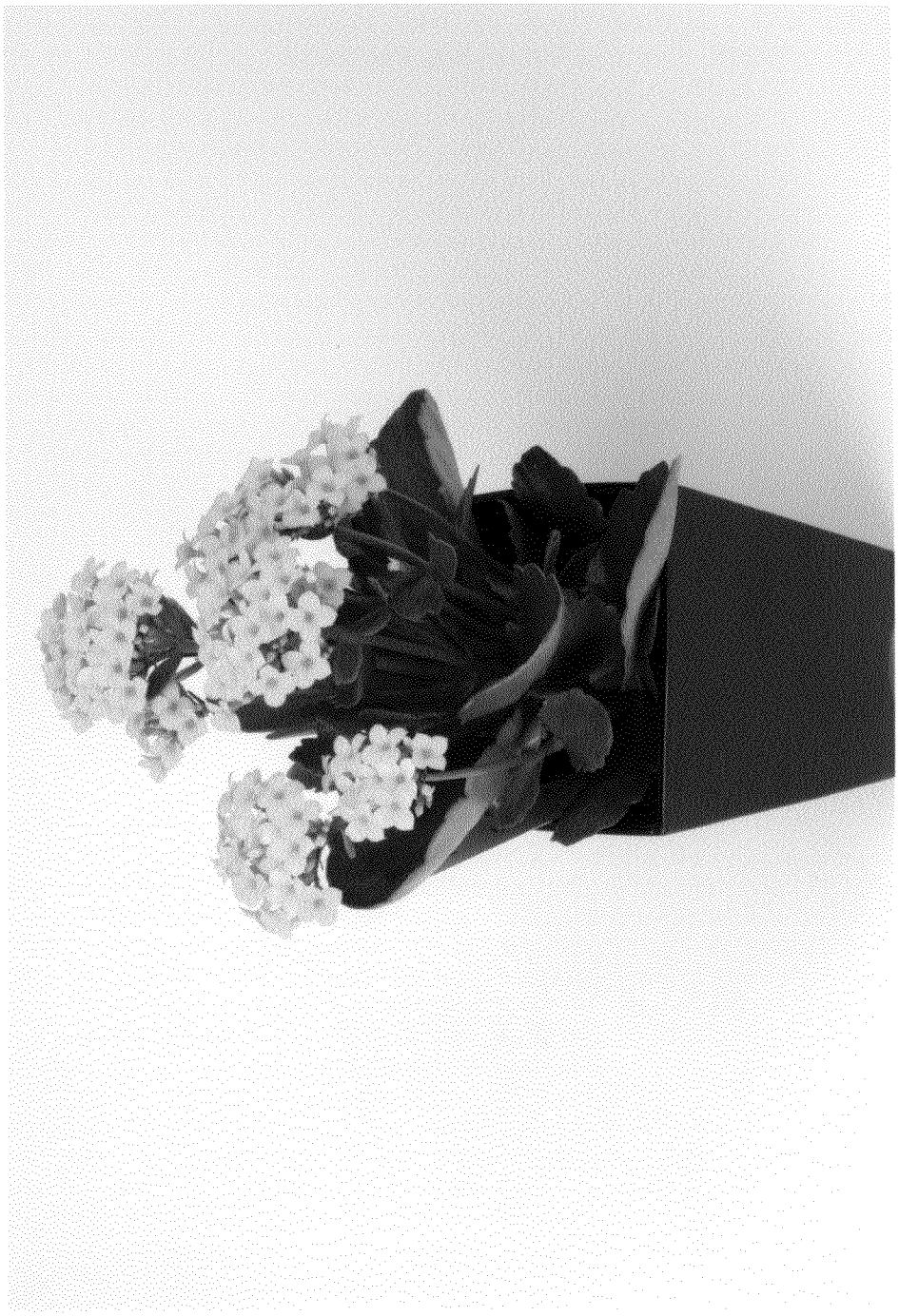

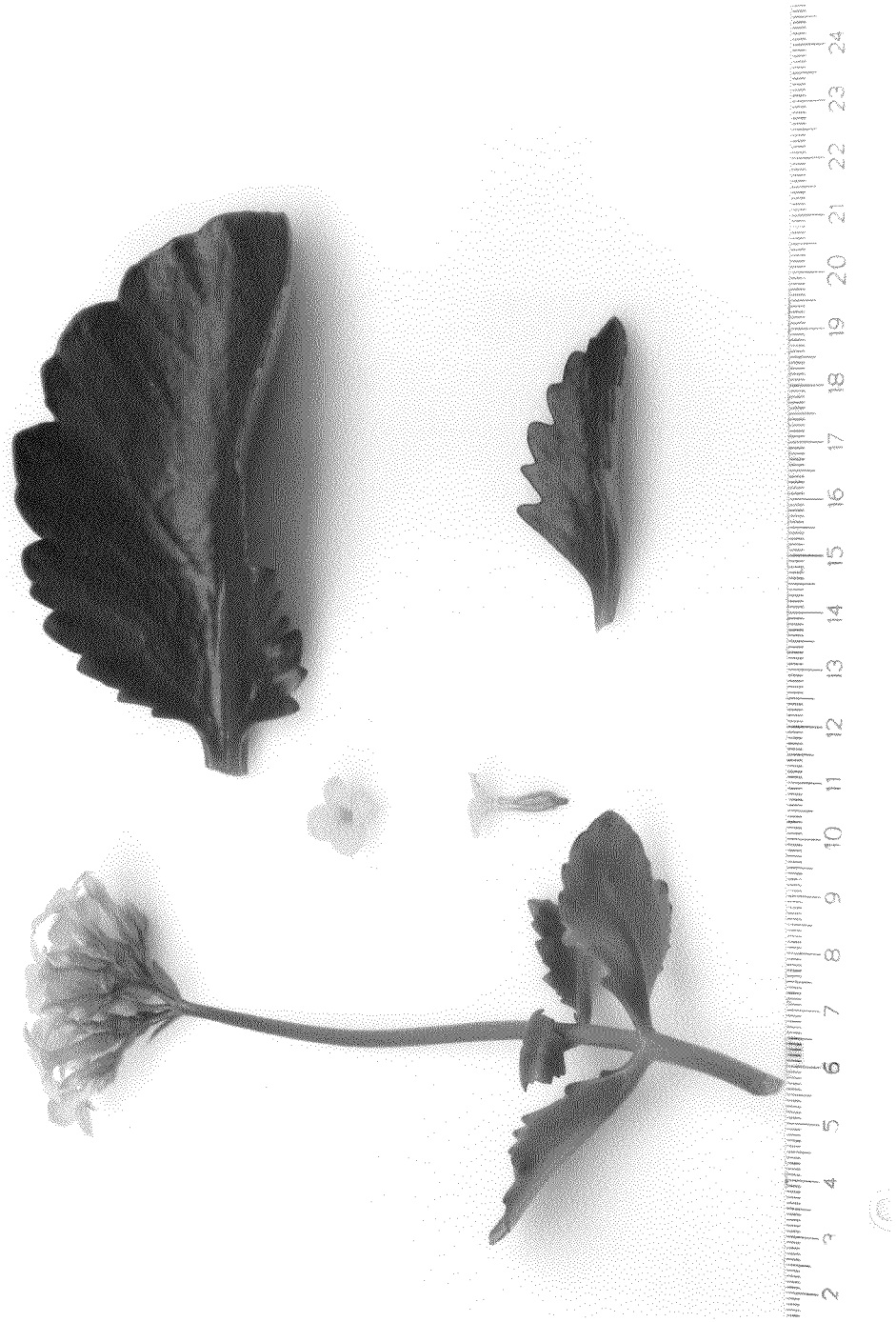
2
3
4
5
6
7
8
9
10
11
12
13
14
15
16
17
18
19
20
21
22
23
24